United States Patent
Harhen et al.

(10) Patent No.: US 6,579,582 B1
(45) Date of Patent: Jun. 17, 2003

(54) APPARATUS AND METHOD FOR FORMING COMPLEX-SHAPED COMPONENTS IN A HEATED POLYMERIC FILM

(75) Inventors: E. Paul Harhen, Duxbury, MA (US); James M. Goddard, Pepperell, MA (US)

(73) Assignee: Vision Sciences Inc., Natick, MA (US)

( * ) Notice: Subject to any disclaimer, the term of this patent is extended or adjusted under 35 U.S.C. 154(b) by 0 days.

(21) Appl. No.: 09/366,950

(22) Filed: Aug. 4, 1999

Related U.S. Application Data (62) Division of application No. 08/948,615, filed on Oct. 10, 1997, now abandoned.

(51) Int. Cl.[7] .............................. A61B 1/005; A61B 1/00
(52) U.S. Cl. ..................... 428/35.2; 428/35.7; 600/101; 600/139; 600/146; 600/175; 600/176; 600/920; 264/292; 264/322; 264/554
(58) Field of Search ............................. 428/35.2, 35.7; 264/554, 291, 292, 320, 322; 600/109, 139, 146, 920, 175, 176, 101

(56) References Cited

U.S. PATENT DOCUMENTS

| | | | |
|---|---|---|---|
| 3,608,016 A | 9/1971 | Loberodi et al. | 264/89 |
| 4,059,380 A | 11/1977 | Judzis et al. | 425/298 |
| 4,123,215 A | 10/1978 | Madenokoji | 425/388 |
| 4,173,392 A * | 11/1979 | Ekinaka et al. | 350/96.26 |
| 4,397,808 A | 8/1983 | Yoshino et al. | 264/521 |
| 4,577,621 A * | 3/1986 | Patel | 600/114 |
| 4,646,722 A | 3/1987 | Silverstein et al. | 128/4 |
| 4,688,554 A * | 8/1987 | Habib | 600/114 |
| 4,869,238 A * | 9/1989 | Opie et al. | 600/109 |
| 4,943,406 A | 7/1990 | Bocchi | 264/522 |
| 5,071,123 A * | 12/1991 | Spector | 446/76 |
| 5,125,143 A * | 6/1992 | Takahashi | 29/237 |
| RE34,110 E * | 10/1992 | Opie et al. | 600/109 |
| 5,318,008 A * | 6/1994 | Bullard | 600/139 |
| 5,337,734 A | 8/1994 | Saab | 128/4 |
| 5,443,781 A | 8/1995 | Saab | 264/291 |
| 5,630,784 A * | 5/1997 | Siegmund et al. | 600/160 |
| 5,685,822 A | 11/1997 | Harhen | 600/125 |
| 5,820,438 A * | 10/1998 | Horton, III | 446/213 |
| 5,902,246 A | 5/1999 | McHenry et al. | 600/476 |

FOREIGN PATENT DOCUMENTS

DE          1454979         5/1969

\* cited by examiner

*Primary Examiner*—Rena Dye
(74) *Attorney, Agent, or Firm*—Dorsey & Whitney LLP

(57) ABSTRACT

A thin-walled polymeric component that may have a selected complex shape, and a method of forming the component. The method includes heating a portion of a polymeric film to a selected malleable temperature, and forming a protrusion in the heated portion while it is malleable. The protrusion defines a protrusion having a first shape. The method also includes positioning a forming tool in the protrusion's interior and drawing a partial vacuum from within the protrusion so as to exert a force on the protrusion and move the protrusion's sidewalls inwardly into engagement with the forming tool. As the partial vacuum is drawn, the protrusion moves to a second shape that may be different than the first shape and that closely conforms to the selected shape of the forming tool. The protrusion is cooled below the malleable temperature and the forming tool is then removed. The distal portion of the protrusion having the selected shape forms the polymeric component, and that distal portion is separated from the remaining portion of the protrusion, thereby providing the thin-walled polymeric component.

63 Claims, 5 Drawing Sheets

APPARATUS AND METHOD FOR FORMING COMPLEX-SHAPED COMPONENTS IN A HEATED POLYMERIC FILM

CROSS-REFERENCE TO RELATED APPLICATION

This application is a divisional of pending U.S. patent application Ser. No. 08/948,615, filed Oct. 10, 1997 now abandoned.

TECHNICAL FIELD

The present invention is directed toward a method of making medical components, and more particularly toward a method of making contoured, thin-walled, complex-shaped medical components usable with intrabody medical devices.

BACKGROUND OF THE INVENTION

The use of intrabody medical equipment, such as endoscopes, catheters, and the like, for diagnostic and therapeutic indications is rapidly expanding. To improve performance, the equipment has been optimized to best accomplish the selected purpose. As an example, endoscopes have been optimized and refined so as to provide upper endoscopes for the examination of the esophagus, stomach, and duodenum, colonoscopes for examining the colon, angioscopes for examining blood vessels, bronchoscopes for examining the bronchii, laparoscopes for examining the peritoneal cavity, arthroscopes for examining joints spaces, nasopharygoscopes for examining nasal passages and pharynx, and intubation scopes for examination of a person's airway.

Optimization of the intrabody medical devices for such therapeutic and diagnostic procedures has resulted in sterile, inexpensive disposable equipment that is used alone or with non-disposable equipment. In the field of endoscopes, a conventional endoscope 10, shown in FIG. 1, has an insertion tube 12 that is connected at its proximal end 14 to a handle or control body 16. The insertion tube 12 is adapted to be inserted into a patient's body cavity to perform a selected therapeutic or diagnostic procedure. The insertion tube 12 contains an imaging system 18 having optical fibers or the like extending along the length of the insertion tube and terminating at a viewing window 19 in the insertion tube's distal end 20. The imaging system 18 conveys an image from the viewing window 19 to an eyepiece 22 on the control body 16 or to a monitor (not shown), so the user can see into a selected body cavity during an endoscopic procedure. The endoscope 10 is described in greater detail in U.S. Pat. No. Re 34,110 and U.S. Pat. No. 4,646,722, which are incorporated by reference herein.

Figure 1:
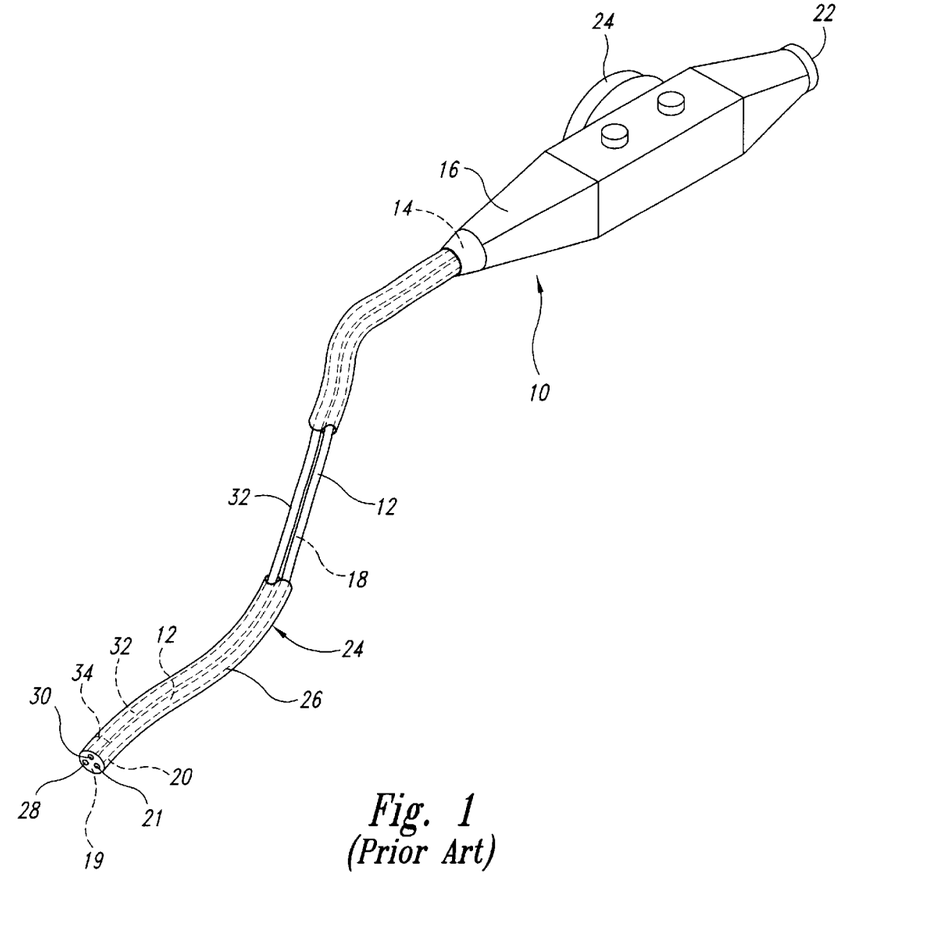
FIG. 1 is an isometric view of a prior art endoscope and endoscopic sheath assembly.

Disposable endoscopic sheath assemblies are used to cover the insertion tube 12 and protect it from being contaminated. Accordingly, the sheath assemblies alleviate the problem and cost of cleaning and sterilizing the. insertion tube 12 between endoscopic procedures. As seen in FIG. 1, a conventional sheath assembly 24, shown partially cut away for illustrative purposes, includes a flexible, elastic sheath 26 that tightly surrounds the endoscope's insertion tube 12. The sheath 26 may also contain one or more working channels 32 that extend along the insertion tube 12 and that are adapted to receive conventional endoscopic accessories therethrough without contaminating the endoscope itself during the endoscopic procedure. The sheath 26 has a distal end portion 21 that includes an endcap 34 having a transparent window 28 positioned to cover the viewing window 19 at the insertion tube's distal end 20 when the sheath assembly is installed. The endcap 34 formed of a relatively rigid material and is sealably secured to the sheath's distal end portion 21.

Endoscopic sheath assemblies used with insertion tubes that have a complex cross-sectional shape, such as C-shaped, often must have an endcap with a corresponding complex cross-sectional shape to snugly fit over the insertion tube's distal end 20. The complex-shaped endcap can be a costly and laborious component to manufacture for the sheath assembly. Other thin-walled components that would be required to have a complex shape if used with endoscopic sheaths or other medical devices having complex shapes may include precision detent mechanisms and short-pitched threads that are manufactured with the necessary accuracy and tolerances required for intricate medical devices.

Figure 2:
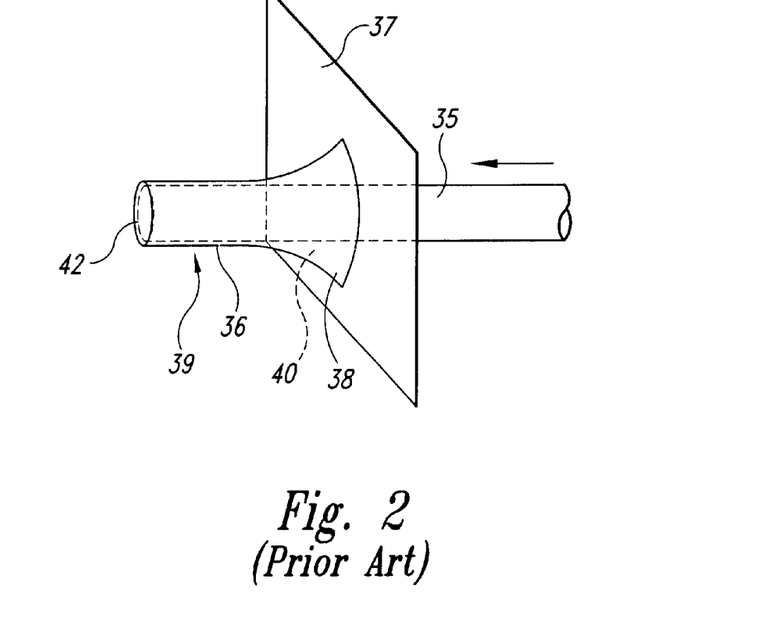
FIG. 2 is an isometric view of a thermal plastic film of the prior art stretched by a mandrel.

U.S. Pat. No. 5,443,781 to Saab teaches a method of forming a disposable sheath with an. optically transparent window that is integral with the sheath. The transparent window is formed so as to maintain a thin-walled, relatively inelastic, yet flexible sheath for an optical medical instrument. Saab teaches forming the sheath by heating a sheet or film of optically transparent polymeric material until the material's viscosity is substantially reduced and the film is malleable. As shown in FIG. 2, a mandrel 35 having a relatively simply cylindrical shape is thrust into the heated film 37 causing the film to stretch and to generally conform to the mandrel's shape. As a result, the heated film 37 is formed into a closed-end sheath 39 having sidewalls 36, a flange or collar 38 at its open proximal end 40, and a closed distal end 42. The mandrel 35 is selected based upon its simple geometrical shape to define the shape of the sheath 39. Accordingly, sheaths having different shapes and sizes are formed using different mandrels with the corresponding shapes and sizes.

The sheath and technique of making the sheath as discussed in Saab, however, results in the film being heated, stretched, and then cooled to remain the shape that generally corresponds to the mandrel's simple. The resulting sheath is limited to having a relatively simple geometrical shape. The method of Saab does not sufficiently allow for making complex-shaped components having close tolerances.

In the design of intrabody medical devices and accessories, including optical and non-optical devices, the need for components having a complex geometry has become more and more apparent. As an example, there is a need for highly-detailed components, such as endcaps, used with more complicated endoscopes. There is further a need for precisely manufactured catheter components or the like with accurately positioned detents or close-pitched threads. Other medical devices and accessories would be benefited by inexpensive thin-walled components with close tolerance demands.

SUMMARY OF THE INVENTION

The present invention provides a method capable of forming complex-shaped medical components in a heated polymeric film to provide thin-walled, durable. low-cost components that may be manufactured to close tolerances, which has been problematic in the prior art. In an exemplary embodiment of the present invention, the method of forming a thin-walled polymeric component includes the steps of heating a portion of the polymeric film to a malleable temperature, and using a forming tool to form a protrusion in the film's heated portion while the polymeric film is malleable. The formed protrusion has an open proximal end, a distal end spaced apart from the proximal end, and sidewalls extending between the proximal and distal ends. The sidewalls and distal end define a first shape of the protrusion and also define an interior of the protrusion. The forming tool has a shaping portion that may have a selected complex shape that is different than the protrusion's first shape. The method further includes the step of exerting a force radially inwardly on the protrusion and moving the protrusion into firm engagement with the forming tool's shaping portion so the protrusion moves from the first shape to a second shape that closely conforms to the selected shape of the forming tool's shaping portion.

In the exemplary embodiment, the radially inward force exerted on the protrusion is achieved by creating a differential pressure so the pressure within the interior of the protrusion is less than the pressure outside the protrusion, thereby causing the protrusion's sidewalls to move inwardly to the second shape. In one embodiment, the step of exerting a differential pressure on the protrusion is achieved by drawing a partial vacuum inside the protrusion. The partial vacuum may be drawn through the forming tool and through at least one vacuum port in the forming tool.

The present invention is also directed toward a polymeric medical component that may have a selected complex shape that is made by the above-described process.

The present invention is also directed toward a vacuum-forming tool capable of forming the medical component from a malleable polymeric protrusion. The vacuum-forming tool includes a shaft having an air passageway and a forming portion, and the forming portion has a shape corresponding to the selected shape of the medical component. The forming portion has an outer surface and a plurality of apertures extending from the outer surface to the air passageway. The shaft is connectable to a vacuum source so the air passageway communicates with the vacuum source to allow the vacuum source to draw air through the apertures into the air passageway, thereby forming a partial vacuum within the malleable polymeric protrusion during the formation of the medical component.

DETAILED DESCRIPTION OF THE INVENTION

Figure 3:
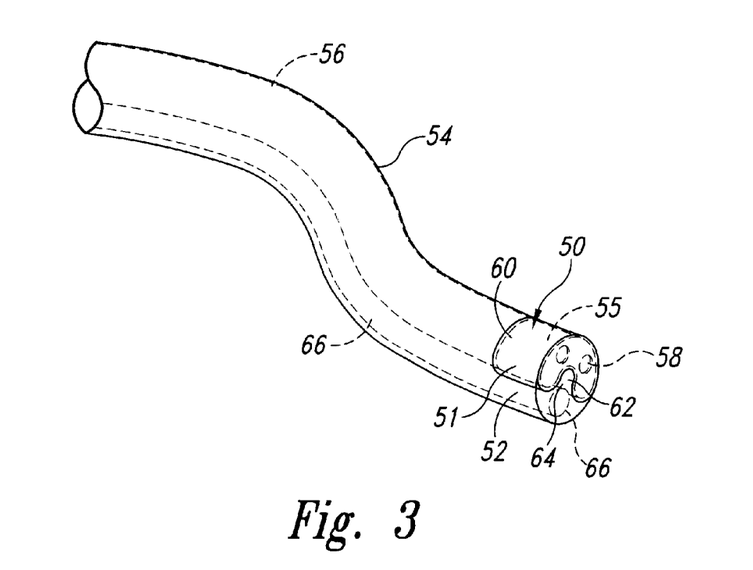
FIG. 3 is an isometric view of a distal portion of an endoscopic sheath having a thin-walled, polymeric endcap formed in accordance with one embodiment of the present invention.

A thin-walled polymeric medical component 50 having a complex shape made in accordance with one embodiment of the present invention is described herein with reference to the attached drawings. An exemplary embodiment of a thin-walled medical component 50, shown in FIG. 3, is attached to a distal end 52 of a sheath 54. The sheath 54 is shaped and sized to receive and isolate, as an example, an endoscope insertion tube 56 shown in phantom lines. The illustrated medical component 50 is a sheath endcap 51 that is sealably attached to the sheath's distal end 52 so as to provide a viewing window therein that allows clear imaging through the endoscope's imaging system 58, also shown in phantom lines.

The distal end portion 55 of the illustrated insertion tube 56 has a generally C-shaped cross-section and the endcap 51 is formed with a corresponding complex geometrical shape that closely conforms to the insertion tube's distal end portion. More specifically, the C-shaped cross-section of the illustrated endcap 51 is defined by a curved outer axial wall 60 that has.a selected radius and a curved inner axial wall 62 that is integrally connected to the outer axial wall 60. The inner axial wall 62 has a radius which is smaller than the radius of the outer axial wall 60. The inner axial wall 62 defines a receiving area 64 that is shaped and sized to receive one or more selected working channels 66, shown in phantom lines, extending through the sheath 54. As an example, the illustrated endoscopic sheath 54 includes a tubular working channel 66 that extends through the sheath and that is sealably connected to the sheath's distal end 52. The tubular working channel 56 snugly fits in the endcap's receiving area 64, while the distal end of the endoscope's insertion tube 56 is snugly received in the endcap 51 between the inner and outer walls. Accordingly, the thin-walled endcap 51 is provided with a complex geometrical shape that receives and retains the insertion tube's distal end therein and retains the working channel 66 adjacent to the distal end while minimizing the cross-sectional area of the sheath and insertion tube combination which is to be inserted into a patient.

While the medical component 50, such as the end cap 51, and the method of making the component is discussed herein with reference to an endoscopic sheath, the method of the present invention is equally applicable to medical components used in procedures for medical devices other than endoscopic procedures. As an example, the medical component 50 in alternate embodiments are complex-shaped components used with catheters, optical medical equipment, and non-optical imaging medical equipment.

The thin-walled polymeric medical component 50 is made by forming a thin polymeric film into the desired shape. The preferred polymeric film used with the present invention is a thermoplastic material including PVC, acrylic, polycarbonate, polyethylene terephthalate, or other thermoplastic polyester material. The polymeric material used by the present invention allows for thin-walled medical components that are substantially inelastic, flexible, and have, high strength, and that can be easily, inexpensively, and quickly manufactured. The polymeric film is selected so the medical component 50 has a wall thickness in the range of approximately 0.0005 to 0.015 inches, inclusive, and preferably in the range of approximately 0.0008 to 0.005 inches, inclusive.

Figure 4:
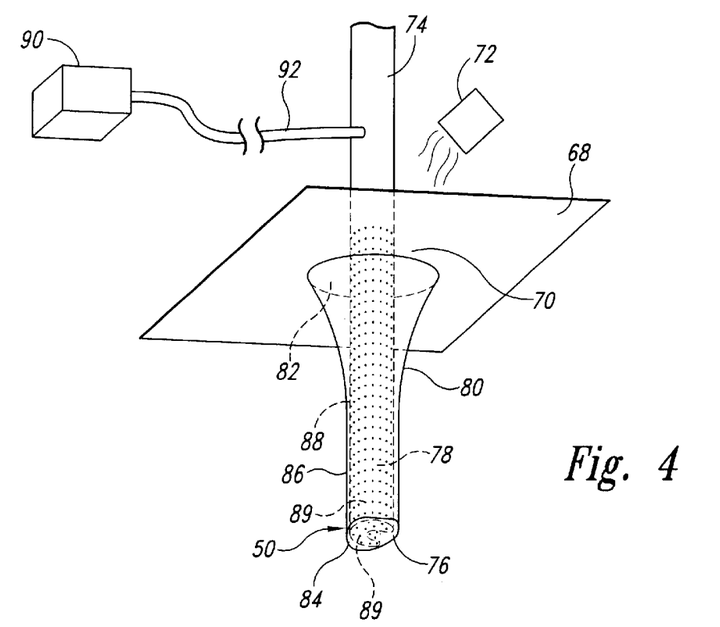
FIG. 4 is an isometric view of a heated thin-walled polymeric film with a funnel-shaped projection formed therein in accordance with one embodiment of the present invention and shown in an extended position, and a complex-shaped forming tool is shown positioned in the protrusion and connected to a vacuum source.
Figure 5:
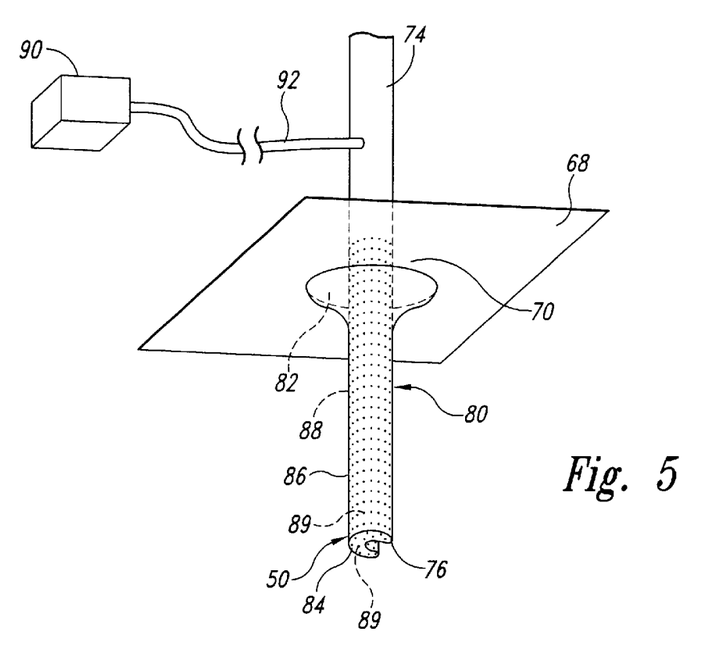
FIG. 5 is an isometric view of the heated polymeric film of FIG. 4 with the projection shown in a contracted position in solid lines on the forming tool, and the projection is shown in the extended position in phantom lines.

In the exemplary embodiment illustrated in FIGS. 3, 4 and 5, the medical component 50 is formed from a material that is optically transparent to visible light. The polymeric film, however, may be selected to provide a desired degree of transparency to electromagnetic radiation in the visible spectrum, or in the non-visible spectrum, e.g., radar, laser, or microwave. The polymeric film may also be selected, when needed, to provide a desired degree of transparency to sound waves, such as for use with ultrasound devices.

As best seen in FIG. 4, the polymeric film 68 is retained in a selected position so as to substantially define a plane. An interior portion of the film 68 is heated by a conventional heating device 72 to a selected malleable temperature to form a malleable, heated portion 70 of the film. The heated portion 70 is then stretched and formed into a protrusion 80, as discussed in greater detail below, by a forming tool 74. The forming tool 74 has a contoured shaping portion 78 with a complex geometrical shape that corresponds to the shape of the endcap or other medical component to be formed. In the illustrated embodiment, the forming tool's shaping portion 78 has a C-shaped cross-section with curved inner and outer surfaces that correspond to the endcap's C-shaped cross-section discussed above.

After the film's heated portion 70 is malleable, the forming tool's shaping portion 78 is pressed into the heated portion generally perpendicular to the plane defined by the film 68, and the forming tool stretches the heated portion away from the plane to form a thin-walled, generally funnel-shaped protrusion 80.

The protrusion 80 has an open proximal end 82, a closed distal end 84 spaced away from the open proximal end and sidewalls 86 extending between the proximal and distal ends. The closed distal end 84 and the sidewalls 86 define an interior 88 of the protrusion 80 that contains the forming tool's shaping portion 78 as the protrusion is formed.

As the protrusion 80 is formed, the protrusion has a generally tubular shape that only roughly conforms to the outer shape of the forming tool's shaping portion 78, but the protrusion's sidewalls 86 do not yet closely conform to the complex shape of the forming tool's shaping portion. As an example, the protrusion's sidewalls 86 conform to the shaping portion's outer curved surface but do not conform to the shaping portion's inner curved surface, such that the protrusion has a generally D-shaped cross-section, rather than the C-shaped cross-section of the shaping portion.

While still malleable, the protrusion's sidewalls 86 and the closed distal end 84 are then brought into firm and close engagement with the forming tool's shaping portion 78, as shown in FIG. 5, thereby closely conforming to the shaping portion's complex geometrical shape. In the exemplary embodiment, the protrusion 80 is brought into firm engagement with the shaping portion 78 by drawing a partial vacuum within the projection's interior 88. The partial vacuum causes a differential pressure in the protrusion that is exerted on the sidewalls 86, so the pressure within the protrusion is less than the pressure outside of the protrusion. Accordingly, the partial vacuum moves the protrusion's sidewalls 86 against the forming tool's shaping portion 78 to achieve the selected complex geometrical shape for the medical component 50. After the protrusion 80 has moved to the contracted position and has cooled from the malleable temperature, the forming tool 74 is removed from the protrusion's interior 88 and the protrusion remains in the contracted position.

As best seen in FIGS. 4 and 5, the forming tool 74 is a partially hollow member with at least one and preferably a plurality of vacuum ports 89 formed in the shaping portion 78. The forming tool 74 is connected to a conventional vacuum source 90 by a vacuum line 92. The vacuum source is adapted to draw air into the forming tool's shaping portion 78 through the vacuum ports 89, thereby creating the partial vacuum within the interior.

Figure 6:
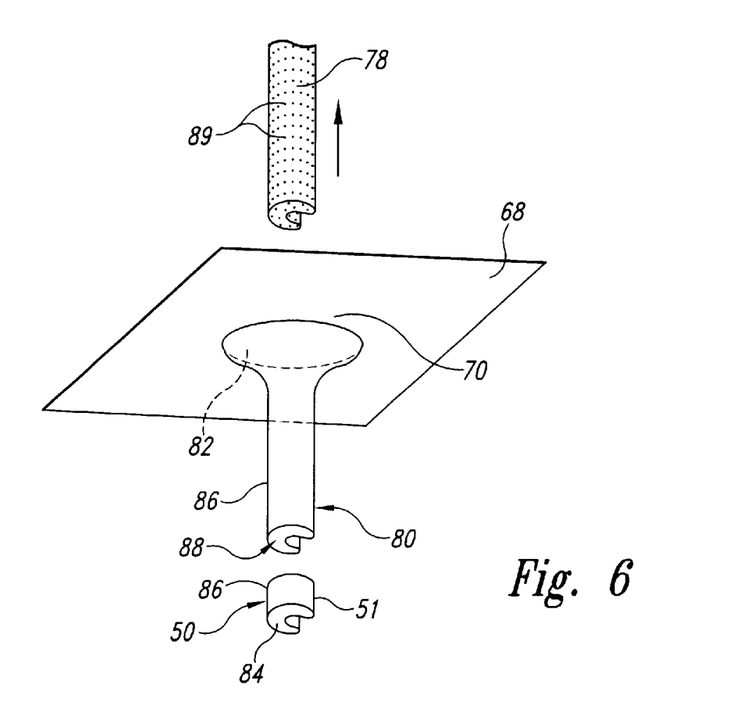
FIG. 6 is an isometric view of the protrusion of FIG. 5 shown with a distal portion of the protrusion being separated from a proximal to provide the selected thin-walled polymeric endcap with complex shape.

As best seen in FIG. 6, after the forming tool 74 is removed, a distal portion of the protrusion 80, which has the complex-shape formed therein, is cut or otherwise separated from the remaining portion of the protrusion, and that distal portion is the thin-walled polymeric medical component 50. The component 50, such as the illustrated C-shaped endcap 51, is then connected to the selected medical device, such as the distal end 52 of the endoscopic sheath 54, as illustrated in FIG. 3.

In an alternate embodiment (not shown), the protrusion 80 is moved to the contracted position by exerting substantially uniform, exterior pressure on the protrusion in a radially inward direction. As an example, the distal portion of the protrusion 80 and the forming tool's shaping portion 78 are positioned, as a unit, within a pneumatic pressure-generating device or other suitable device that exerts the exterior pressure, and the pressure generating device moves the protrusion's sidewalls 86 from the expanded position to the contracted position and into close engagement with the forming tool's shaping portion 78. Accordingly, the radially inward directed forces on the protrusion 80 may be achieved by generating a vacuum in the protrusion's interior or by creating a pressure external to the protrusion. The preferred method, however, is to use the partial vacuum within the protrusion's interior 88 because the partial vacuum does not disturb the temperature profile of the heated polymeric film.

Figure 7:
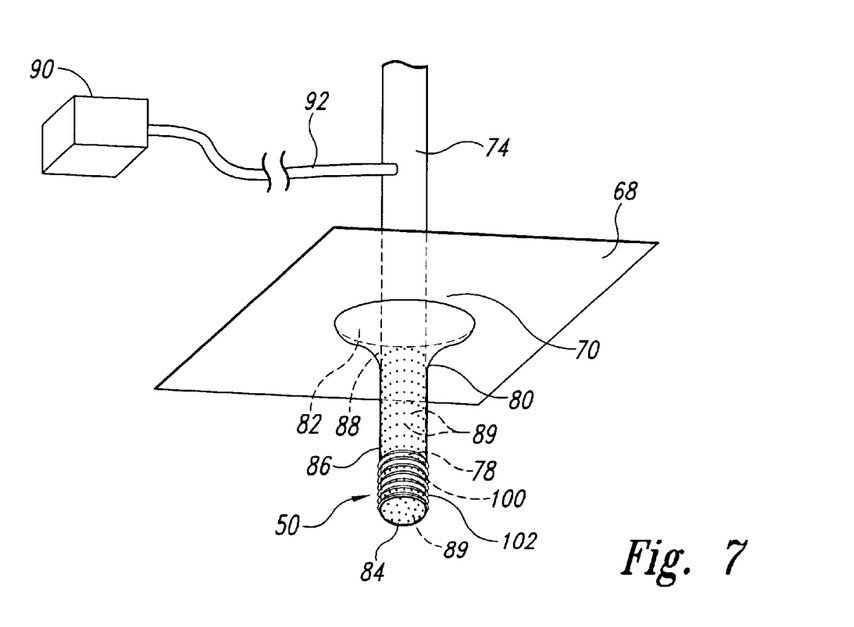
FIG. 7 is an isometric view of an alternate embodiment of the present invention with the thin-walled component having close-pitched threads formed therein by a complex-shaped threaded forming tool shown in phantom lines.

In addition to forming medical components having complex contoured shapes, such as the C-shape cross-sectional shape, the disclosed embodiment of the present invention also allows easy and inexpensive formation of a thin-walled, polymeric medical component 50 having close-pitched, accurately-located threads formed therein. As best seen in FIG. 7, the forming tool 74 has a plurality of close-pitched threads 100 formed in the shaping portion 78. The forming tool 74 is pressed into the heated portion 70 of the polymeric film 68 when at malleable temperature, thereby forming the protrusion 80. Accordingly, the protrusion's sidewalls 86 are generally adjacent to the threads 100 on the forming tool 74, but do not yet closely conform to the threads. The differential pressure is then generated in the protrusion's interior 88, moving the sidewalls 86 to the contracted position and into close engagement with the threads 100, thereby forming the close-pitched, accurately positioned threads 102 in the protrusion. The forming tool 74 is then removed preferably by rotating it so the shaping portion 78 unscrews from the threads 102 formed in the protrusion 80.

Figure 8:
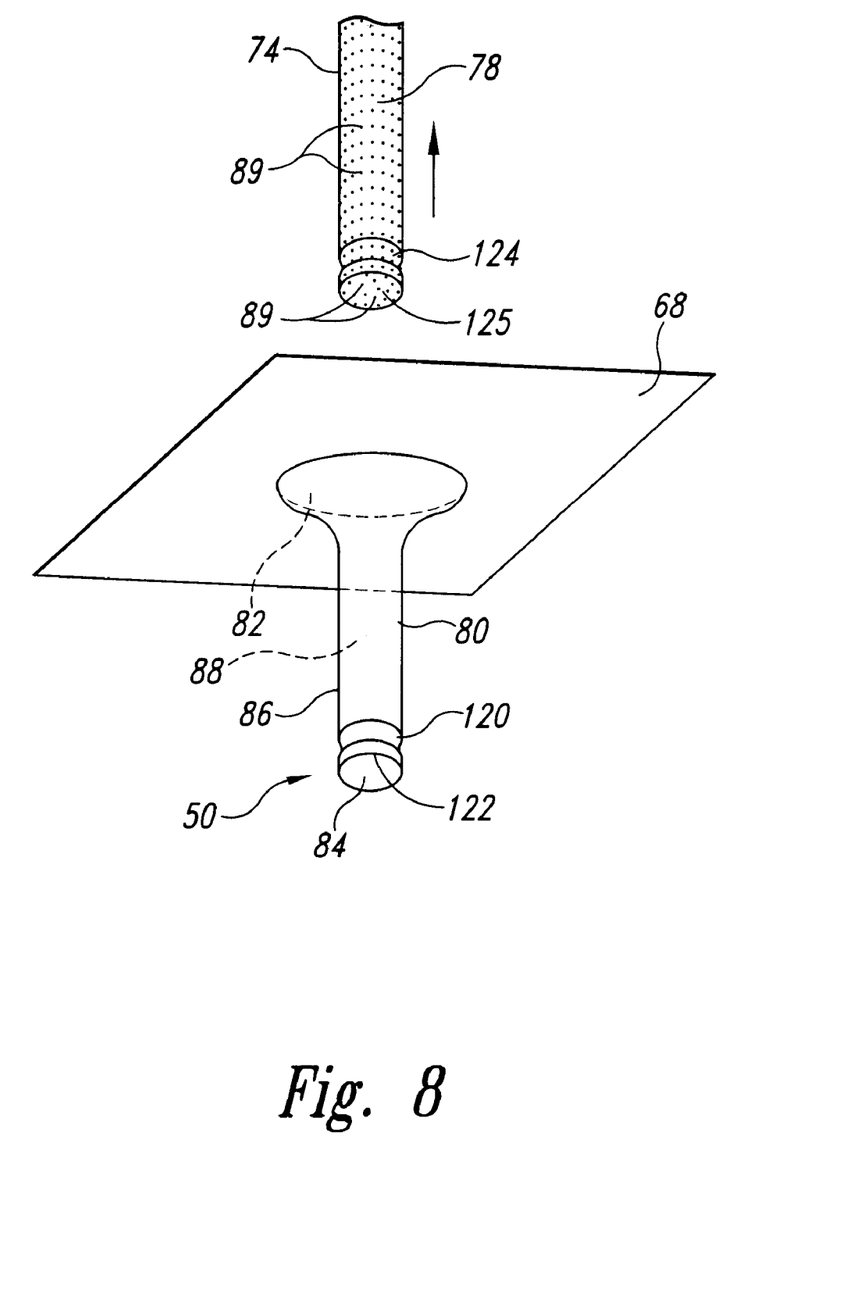
FIG. 8 is an isometric view of an alternate embodiment of the present invention with the thin-walled component having detents formed therein by a forming tool shown in phantom lines.

The present invention also allows for easy and inexpensive formation of a thin-walled polymeric medical component 50, as shown in FIG. 8, having precisely located detents 120 formed in selected positions that correspond to detent receiving portions on a selected medical device, not shown. The medical component 50 may also have a concave-shaped distal end 122 that follows the contour of the selected medical device. The medical component 50 illustrated in FIG. 8 is formed using a forming tool 74 with a shaping portion 78 having one or more detent molds 124 in a selected position and having a concave distal end surface 125. The shaping portion 78 also has the vacuum ports 89 formed therein for creating the partial vacuum in the protrusion's interior portion 88. Accordingly, when the forming tool 74 is pressed into the film's heated portion 70 to form the protrusion 80 and the partial vacuum is drawn through the vacuum ports 89, the protrusion's sidewalls 86 are drawn into firm engagement with the forming tool's detent molds 124 so as to form the detents 120 in the protrusion. Similarly, the protrusion's closed distal end 84 is drawn into firm engagement with the forming tool's concave distal end 125, thereby forming a medical component 50 with a concave closed distal end.

After the polymeric material is cooled, the forming tool 74 is removed from the protrusion's interior 88 and the selected shaping portion of the protrusion 80 is cut in order to remove the complex-shaped medical component 50 from the rest of the protrusion. In the embodiment wherein a detent or the like is formed in the medical component 50, the forming tool 74 may be removed from the protrusion's interior 88 by slightly deflecting the sidewalls 86 of the protrusion 80 until sufficient clearance is provided between the sidewalls and the forming tool's shaping portion 78. Such deflection is possible because the thin-walled polymeric material is sufficiently flexible to move so as to allow removal of the forming tool without permanent deformation of the medical component 50.

In alternate embodiments, the thin-walled polymeric medical component 50 is formed by stretching or drawing the protrusion 80 in two or more steps, so selected portions of the component have a different thickness than the thickness of other portions of the component. In one embodiment, an endcap with an integral optical lens is formed by pressing a first forming tool 74 into the heated portion 70 to form the protrusion 80, and the differential pressure is applied to the protrusion, as discussed above. The first forming tool 74 is specifically designed to form the lens of the endcap to provide the selected thickness and optical characteristics of the lens.

After the lens is formed, the first forming tool is removed from the protrusion 80. While the protrusion 80 is still malleable, a second forming tool is pressed into the protrusion to further draw or stretch the protrusion's sidewalls 86 to form thinner sidewalls. The second forming tool is designed to support the lens portions so there is substantially no further drawing of the lens while the sidewalls 86 are being drawn. The differential pressure is exerted on the protrusion so the protrusion conforms to the second forming tool, and the second forming tool is then removed. Accordingly the lens maintains its selected thickness, and the sidewalls are thinner than when formed by the first forming tool.

In another one of the alternate embodiments, the protrusion 80 is formed with portions having different thicknesses by heating the film 68 a first time and forming the protrusion with a forming tool as discussed above. The protrusion 80 is then allowed to cool to below the malleable temperature. A selected portion of the protrusion 80, such as the sidewalls 86, is heated a second time to the malleable temperature, and the sidewalls or other selected portion is further stretched or drawn with the same or a different forming tool. Accordingly, the protrusion's selected portion that is reheated and further drawn is thinner while the protrusion's other portions that were not heated a second time are not further thinned by the second drawing process. If further drawing is needed at other specific portions of the protrusion 80, additional steps of heating and drawing can be performed to achieve the specific size, thickness, and characteristics of the component 50. In another alternate embodiment (not shown), the thin-walled polymeric medical component 50 is formed by pressing the forming tool 74 into the polymeric film's heated portion 70, such that the distal end of the forming tool pierces the distal end of the protrusion. In this alternate embodiment, the protrusion's sidewalls are substantially sealably connected to the forming tool's shaping portion 78, so a partial vacuum can still be generated to draw the sidewalls into firm engagement with the shaping portion.

In yet another embodiment (not shown), the complex-shaped medical component 50 is further modified or machined after formation of the component so as to remove or modify a selected portion of the medical component. As an example, polymeric material is removed from a distal end portion of a selected medical component to allow a selected medical device to be positioned partially within the component, while a selected portion of the device extends through the thin-walled polymeric medical component. Accordingly, the thin-walled, polymeric medical component can be formed with a selected complex shape for use with a wide range of medical devices.

From the foregoing it will be appreciated that, although specific embodiments of the invention have been described herein for purposes of illustration, various modifications may be made without deviating from the spirit and scope of the invention. Also, although the various embodiments of the invention have been described as being used to form complex components, it will be understood that relatively simple components may also be formed in accordance with the invention. Accordingly, the invention is not limited except as by the appended claims.

what is claimed is:

1. A polymeric medical component having a selected shape made by a process comprising:

heating a sheet of polymeric film to a malleable temperature to form a malleable heated portion;

forming a protrusion in the heated portion while malleable, the protrusion having an open proximal end, a distal end, and sidewalls extending between the proximal and distal ends, the sidewalls and distal end defining a first shape of the protrusion;

positioning a forming tool in an interior of the protrusion, the forming tool having a shaping portion with a selected shape that is different than the first shape of the protrusion, and wherein the shaping portion includes a detent mold circumferentially disposed thereon;

exerting a force on the protrusion to move a portion of the protrusion inwardly into engagement with the forming tool's shaping portion so the protrusion changes from the first shape to a second shape that conforms to the selected shape of the forming tool's shaping portion, including moving the sidewalls into engagement with the detent mold to form a detent member circumferentially disposed on an inner surface of the sidewalls that conforms to the detent mold on the shaping portion; and forming an aperture in the distal end of the protrusion.

2. The medical component of claim 1 wherein exerting a force includes exerting a differential pressure on the protrusion so the pressure within the protrusion is less than the pressure exterior of the protrusion to cause the protrusion to change to the second shape.

3. The medical component of claim 1 wherein the process further includes cooling the protrusion to a temperature below the malleable temperature, and removing the forming tool from the protrusion after the heated protrusion has cooled to the temperature below the malleable temperature.

4. The component of claim 1 wherein the shaping portion has a plurality of first threads thereon and wherein exerting a force on the protrusion includes moving the sidewalls into engagement with the first threads to form a plurality of second threads on the inner surface of the sidewalls that conform to the first threads on the shaping portion.

5. The component of claim 1 wherein the distal end of the protrusion includes an at least partially transparent portion, and wherein forming an aperture in the distal end of the protrusion includes, forming an aperture in the at least partially transparent portion.

6. The component of claim 1 wherein the process further includes cooling the protrusion to a temperature below the malleable temperature, and after cooling, heating a selected portion of the protrusion to the malleable temperature and changing the thickness of the selected portion of the protrusion from a first thickness to a second thickness that is less than the first thickness.

7. The component of claim 1 wherein the process further includes removing the forming tool from the protrusion after the protrusion has changed to the second shape, and inserting a second forming tool into the protrusion and changing the thickness of a selected portion of the protrusion from a first thickness to a second thickness that is less than the first thickness.

8. The component of claim 1 wherein the process further comprises separating the first shape of the protrusion from the second shape after the protrusion is in the second position, wherein the first shape defines the thin-walled polymeric component having the selected shape.

9. The component of claim 1 wherein exerting a force on the protrusion includes reducing an interior pressure within at least a portion of the interior of the protrusion so the pressure within the portion of the protrusion is less than the pressure exterior of the portion of the protrusion to cause the portion of the protrusion to change to the second shape.

10. The component of claim 1 wherein forming a protrusion in the heated portion includes forming a protrusion in the heated portion while malleable, the protrusion having an open proximal end, a distal end, and sidewalls having a thickness in the range of 0.0005 inches to 0.015 inches extending between the proximal and distal ends.

11. The component of claim 1 wherein heating a sheet of polymeric film includes heating a sheet of polymeric film that is optically transparent to visible light.

12. The component of claim 1 wherein heating a sheet of polymeric film includes heating a sheet of polymeric film that is at least partially transparent to sound waves.

13. The component of claim 1 wherein the distal end of the protrusion comprises an optical lens.

14. A polymeric component formed by a process comprising:
beating at least a portion of a polymeric film to form a malleable portion;
forming a protrusion in the malleable portion;
positioning a forming tool in an interior of the protrusion, the forming tool having a shaping portion, wherein the shaping portion includes an externally-threaded portion having an external thread disposed thereon and positioned within the interior of the protrusion, wherein positioning a forming tool in an interior of the protrusion comprises positioning a forming tool that includes .a segment having a concave cross-sectional shape within the interior of the protrusion; and forcing at least a portion of the protrusion into substantially conforming engagement with the shaping portion so the at least portion of the protrusion substantially adopts a cross-sectional shape of the shaping portion and conforms to the externally-threaded portion on the shaping portion and forms an internal thread disposed on an inner surface of the protrusion, wherein forcing at least a portion of the protrusion into substantially conforming engagement comprises forcing at least a portion of the protrusion into substantially conforming engagement with concave cross-sectionally shaped segment of the shaping tool.

15. The component of claim 14 wherein heating at least a portion of a polymeric film includes heating at least a portion of a polymeric film that is optically transparent to visible light.

16. The component of claim 14 wherein heating at least a portion of a polymeric film includes heating at least a portion of a polymeric film that is at least partially transparent to sound waves.

17. The component of claim 14 wherein forming a protrusion in the malleable portion comprises forming a protrusion in the malleable portion having an open proximal end, a distal end, and at least one sidewall extending between the proximal and distal ends.

18. The component of claim 14 wherein forming a protrusion in the malleable portion comprises forming a protrusion in the malleable portion having an open proximal end, a distal end, and at least one sidewall having a thickness in the range of 0.0005 inches to 0.015 inches extending between the proximal and distal ends.

19. The component of claim 14 wherein positioning a forming tool in an interior of the protrusion comprises positioning a forming tool that includes an approximately C-shaped cross-sectionally shaped portion.

20. The component of claim 14 wherein positioning a forming tool in an interior of the protrusion comprises positioning a forming tool that includes a detent-shaped portion circumferentially-disposed thereabout within the interior of the protrusion, and wherein forcing at least a portion of the protrusion into substantially conforming engagement with the shaping portion includes forcing the portion of the protrusion into engagement with the detent-shaped portion to form a detent member circumferentially-disposed on an inner surface thereof.

21. The component of claim 14 wherein forcing at least a portion of the protrusion into substantially conforming engagement comprises exerting a differential pressure on at least a portion of the protrusion so an interior pressure within at least a portion of the protrusion is less than an exterior pressure thereon.

22. The component of claim 14 wherein forcing at least a portion of the protrusion into substantially conforming engagement comprises reducing an interior pressure within at least a portion of the protrusion so the interior pressure within at least a portion of the protrusion is less than an exterior pressure thereon.

23. The component of claim 14 wherein the segment of the forming tool having a concave cross-sectional shape comprises a substantially C-shaped cross-section defined by a first outer axial surface ,with a first radius and a second outer axial surface with a second radius that is smaller than the first radius.

24. The component of claim 14 wherein the process further comprises separating a first portion of the protrusion from a second portion of the protrusion, the first portion being the component.

25. The component of claim 14 wherein the process further comprises forming an aperture in the distal end of the protrusion.

26. The component of claim 14 wherein the process further comprises cooling the protrusion to a non-malleable temperature.

27. The component of claim 14 wherein the process further comprises:
cooling the protrusion to a non-malleable temperature;
after cooling, reheating a selected portion of the protrusion to the malleable temperature; and
changing a thickness of a sidewall of the selected portion.

28. The component of claim 14 wherein the process further comprises:
removing the forming tool from the protrusion; and
inserting a second forming tool into the protrusion.

29. The component of claim 28 wherein the process further comprises changing a thickness of a selected portion of the protrusion from a first thickness to a second thickness that is less than the first thickness.

30. The component of claim 28 wherein the process further comprises:
reheating a selected portion of the protrusion to the malleable temperature;
positioning a second shaping portion in the interior of the selected portion of the protrusion; and
forcing at least a portion of the selected portion of the protrusion into substantially conforming engagement with the second shaping portion so at least a portion of the selected portion of the protrusion substantially adopts a cross-sectional shape of the second shaping portion.

31. The component of claim 28 wherein the process further comprises:
forcing at least a portion of the protrusion into substantially conforming engagement with a second shaping portion so at least a portion of the protrusion substantially adopts a cross-sectional shape of the second shaping portion.

32. The component of claim 14 wherein the protrusion includes a distal end comprising an optical lens.

33. The component of claim 14 wherein the protrusion includes a distal end comprising a transparent window.

34. A polymeric medical component having a cross-sectional shape that includes a concave portion made by the process of:
heating a sheet of polymeric film to a malleable temperature to form a malleable heated portion;
forming a protrusion in the heated portion while malleable, the protrusion having an open proximal end, a distal end, and sidewalls extending between the proximal and distal ends, the sidewalls and distal end defining a first shape of the protrusion;
positioning a forming tool in an interior of the protrusion, the forming tool having a shaping portion with a selected shape that is different than the first shape of the protrusion, the shaping portion of the forming tool including a segment having a concave cross-sectional shape; and
exerting a force on the protrusion to move a portion of the protrusion inwardly into engagement with the forming tool's shaping portion so the protrusion changes from the first shape to a second shape that conforms to the selected shape of the forming tool's shaping portion, wherein at least part of the protrusion has a cross-sectional shape that conforms with the concave cross-sectional shape.

35. The medical component of claim 34 wherein positioning a forming tool in an interior of the protrusion comprises positioning a forming tool in an interior of the protrusion, wherein the segment of the shaping portion of the forming tool having a concave cross-sectional shape comprises a substantially C-shaped cross-section.

36. The medical component of claim 34 wherein the process step of exerting a force includes exerting a differential pressure on the protrusion so the pressure within the protrusion is less than the pressure exterior of the protrusion to cause the protrusion to change to the second shape.

37. The medical component of claim 34 wherein the forming tool's shaping portion includes a detent mold thereon, and the process includes the step of exerting a force on the protrusion includes moving the sidewalls into engagement with the detent mold to form a detent member in the sidewalls that conforms to the detent mold on the forming tool's shaping portion.

38. The component of claim 34 wherein the process further includes the step of forming an aperture in the distal end of the protrusion.

39. The component of claim 34 wherein the forming tool's shaping portion has a plurality of first threads thereon and the process step of exerting a force on the protrusion includes moving the protrusion's sidewalls into engagement with the first threads to form a plurality of second threads in the sidewalls that conform to the first threads on the forming tool's shaping portion.

40. The component of claim 34 wherein the distal end of the protrusion is a closed distal end defining an optically transparent viewing window connectable to an endoscopic sheath.

41. The component of claim 34 wherein the distal end of the protrusion comprises an optical lens.

42. The component of claim 34 wherein the distal end of the protrusion comprises a closed distal end including a transparent window.

43. The component of claim 34 wherein the process further includes the steps of cooling the protrusion to a temperature below the malleable temperature, and after the cooling step heating a selected portion of the protrusion to the malleable temperature and changing the thickness of the selected portion of the protrusion from a first thickness to a second thickness that is less than the first thickness.

44. The component of claim 34 wherein the process further includes the steps of removing the forming tool from the protrusion after the protrusion has changed to the second shape, and inserting a second forming tool into the protrusion and changing the thickness of a selected portion of the protrusion from a first thickness to a second thickness that is less that the first thickness.

45. A polymeric medical component having a selected shape made by a process comprising:
heating a sheet of polymeric film to a malleable temperature to form a malleable heated portion;
forming a protrusion in the heated portion while malleable, the protrusion having an open proximal end, a distal end, and sidewalls extending between the proximal and distal ends, the sidewalls and distal end defining a first shape of the protrusion, and wherein the distal end of the protrusion comprises an optical lens;
positioning a forming tool in an interior of the protrusion, the forming tool having a shaping portion with a selected shape that is different than the first shape of the protrusion, and wherein the shaping portion includes a detent mold circumferentially disposed thereon; and exerting a force on the protrusion to move a portion of the protrusion inwardly into engagement with the forming tool's shaping portion so the protrusion changes from the first shape to a second shape that conforms to the selected shape of the forming tool's shaping portion, including moving the sidewalls into engagement with the detent mold to form a detent member circumferentially disposed on an inner surface of the sidewalls that conforms to the detent mold on the shaping portion.

46. The medical component of claim 45 wherein exerting a force includes exerting a differential pressure on the protrusion so the pressure within the protrusion is less than the pressure exterior of the protrusion to cause the protrusion to change to the second shape.

47. The medical component of claim 45 wherein the process further includes cooling the protrusion to a temperature below the malleable temperature, and removing the forming tool from the protrusion after the heated protrusion has cooled to the temperature below the malleable temperature.

48. The component of claim 45 wherein the process further includes forming an aperture in the distal end of the protrusion.

49. The component of claim 45 wherein the shaping portion has a plurality of first threads thereon and wherein exerting a force on the protrusion includes moving the sidewalls into engagement with the first threads to form a plurality of second threads on the inner surface of the sidewalls that conform to the first threads on the shaping portion.

50. The component of claim 45 wherein the process further includes cooling the protrusion to a temperature below the malleable temperature, and after cooling, heating a selected portion of the protrusion to the malleable temperature and changing the thickness of the selected portion of the protrusion from a first thickness to a second thickness that is less than the first thickness.

51. The component of claim 45 wherein the process further includes removing the forming tool from the protrusion after the protrusion has changed to the second shape, and inserting a second forming tool into the protrusion and changing the thickness of a selected portion of the protrusion from a first thickness to a second thickness that is less than the first thickness.

52. The component of claim 45 wherein the process further comprises separating the first shape of the protrusion from the second shape after the protrusion is in the second position, wherein the first shape defines the thin-walled polymeric component having the selected shape.

53. The component of claim 45 wherein exerting a force on the protrusion includes reducing an interior pressure within at least a portion of the interior of the protrusion so the pressure within the portion of the protrusion is: less than the pressure-exterior of the portion of the protrusion to cause the portion of the protrusion to change to the second shape.

54. The component of claim 45 wherein forming a protrusion in the heated portion includes forming a protrusion in the heated portion while malleable, the protrusion having an open proximal end, a distal end, and sidewalls having a thickness in the range of 0.0005 inches to 0.015 inches extending between the proximal and distal ends.

55. The component of claim 45 wherein heating a sheet of polymeric film includes heating a sheet of polymeric film that is optically transparent to visible light.

56. The component of claim 45 wherein heating a sheet of polymeric film includes heating a sheet of polymeric film that is at least partially transparent to sound waves.

57. A polymeric component formed by a process comprising:
heating at least a portion of a polymeric film to form-a malleable portion;
forming a protrusion in the malleable portion;
positioning a forming tool in an interior of the protrusion, the forming tool having a shaping portion, wherein the shaping portion includes an externally-threaded portion having an external thread disposed thereon and positioned within the interior of the protrusion; and
forcing at least a portion of the protrusion into substantially conforming engagement with the shaping portion so the at least portion of the protrusion substantially adopts a cross-sectional shape of the shaping portion and conforms to the externally-threaded portion on the shaping portion and forms an internal thread disposed on an inner surface of the protrusion, wherein the protrusion includes a distal end comprising a transparent window.

58. The component of claim 57 wherein heating at least a portion of a polymeric film includes heating at least la portion of a polymeric film that is optically transparent to visible light.

59. The component of claim 57 wherein positioning a forming tool in an interior of the protrusion comprises positioning a forming tool that includes a detent-shaped portion circumferentially-disposed thereabout within the interior of the protrusion, and wherein forcing at least a portion of the protrusion into substantially conforming engagement with the shaping portion includes forcing the portion of the protrusion into engagement with the detent-shaped portion to form a detent member circumferentially-disposed on an inner surface thereof.

60. The component of claim 57 forcing at least a portion of the protrusion into substantially conforming engagement comprises exerting a differential pressure on at least a portion of the protrusion so an interior pressure within at least a portion of the protrusion is less than an exterior pressure thereon.

61. The component of claim 57 wherein positioning a forming tool in an interior of the protrusion comprises positioning a forming tool that includes a segment having a concave cross-sectional shape within the interior of the protrusion.

62. The component of claim 57 wherein the segment of the forming tool having a concave cross-sectional shape comprises a substantially C-shaped cross-section.

63. The component of claim 57 wherein the transparent window comprises an optical lens.

* * * * *

UNITED STATES PATENT AND TRADEMARK OFFICE
CERTIFICATE OF CORRECTION

PATENT NO. : 6,579,582 B1
DATED : June 17, 2003
INVENTOR(S) : E. Paul Harhen and James M. Goddard It is certified that error appears in the above-identified patent and that said Letters Patent is hereby corrected as shown below:

Column 1,
Line 31, reads "for examining joints" should read -- for examining joint --
Line 57, reads "sterilizing the. insertion" should read -- sterilizing the insertion --

Column 2,
Line 3, reads "endcap 34 formed of a" should read -- endcap 34 is formed of a --
Line 19, reads "with an. optically" should read -- with an optically --
Line 41, reads "mandrel's simple." should read -- mandrel's simple shape. --

Column 3,
Line 64, reads "proximal to provide" should read -- proximal portion to provide --

Column 4,
Line 30, reads "that has.a selected" should read -- that has a selected --
Line 66, reads "and have," should read -- and have --

Column 7,
Line 12, reads "forming tool's.concave" should read -- forming tool's concave --

Column 9,
Line 13, reads "includes, forming" should read -- includes forming --
Line 66, reads ".a segment having" should read -- a segment having --

Column 10,
Line 11 reads "with concave" should read -- with a concave --
Line 61, reads "axial surface ,with" should read -- axial surface with --

Column 12,
Line 16, reads "protrusion includes" should read -- protrusion including --

Column 13,
Line 53, reads "protrusion is: less than" should read -- protrusion is less than --

UNITED STATES PATENT AND TRADEMARK OFFICE
CERTIFICATE OF CORRECTION

PATENT NO. : 6,579,582 B1
DATED : June 17, 2003
INVENTOR(S) : E. Paul Harhen and James M. Goddard It is certified that error appears in the above-identified patent and that said Letters Patent is hereby corrected as shown below:

<u>Column 14,</u>
Line 11, reads "to form-a" should read -- to form a --
Line 29, reads "at least la" should read -- at least a --
Line 42, reads "claim 57 forcing' should read -- claim 57 wherein forcing --

Signed and Sealed this

Sixth Day of July, 2004

JON W. DUDAS
*Acting Director of the United States Patent and Trademark Office*